United States Patent [19]
Burton et al.

[11] Patent Number: 5,919,925
[45] Date of Patent: Jul. 6, 1999

[54] 2-ISOCEPHEM AND OXACEPHEM DERIVATIVES AND USE AS ANTIBACTERIAL AGENTS

[75] Inventors: George Burton, Wallington; Brian Charles Gasson, Redhill; Stephen Christopher Martin Fell, Horsham, all of United Kingdom

[73] Assignee: Pfizer Inc., New York, N.Y.

[21] Appl. No.: 08/949,773

[22] Filed: Oct. 14, 1997

Related U.S. Application Data

[62] Continuation of application No. 08/694,731, Aug. 9, 1996, abandoned, which is a division of application No. 08/256,677, filed as application No. PCT/GB93/00068, Jan. 14, 1993, Pat. No. 5,578,591.

[30] Foreign Application Priority Data

Jan. 22, 1992 [GB] United Kingdom ............... 9201290
Jan. 22, 1992 [GB] United Kingdom ............... 9201291
Jan. 14, 1993 [WO] WIPO ............... PCT/GB93/00068

[51] Int. Cl.$^6$ ............... C07D 501/48; C07D 498/04
[52] U.S. Cl. ............... 540/300; 540/214; 540/215; 540/200
[58] Field of Search ............... 540/205, 214, 540/215, 300, 200, 364

[56] References Cited

U.S. PATENT DOCUMENTS 4,440,682  4/1984  Bose et al. ............... 260/239 A
5,578,591  11/1996  Burton et al. ............... 514/210

OTHER PUBLICATIONS

Mastalerz et al. J. Med. Chem., 1988, 31, pp. 1190–1196.

*Primary Examiner*—Mukund J. Shah
*Assistant Examiner*—Pavanaram K. Sripada
*Attorney, Agent, or Firm*—P. C. Richardson; P. H. Ginsburg; L. B. Ling

[57] ABSTRACT

Compounds of formula (I) or salts thereof:

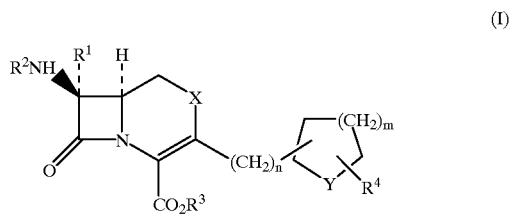

wherein $R^1$ is hydrogen, methoxy or formamido; $R^2$ is an acyl group; $CO_2R^3$ is a carboxy group or a carboxylate anion, or $R^3$ is a carboxy protecting group, pharmaceutically acceptable salt-forming group or in vivo hydrolysable ester group; $R^4$ represents hydrogen or up to four substituents; X is O, S, SO or $SO_2$; Y is O, S, SO or $SO_2$; n is 0 or 1; and m is 1 or 2. The compounds have antibacterial activity. Methods of synthesis of, and pharmaceutical formulations containing, compounds (I) are also described.

2 Claims, No Drawings

2-ISOCEPHEM AND OXACEPHEM DERIVATIVES AND USE AS ANTIBACTERIAL AGENTS

This is a continuation of application Ser. No. 08/694,731, filed on Aug. 9, 1996, now abandoned; which is a division of 08/256,677 filed Jul. 20, 1994, which is a 371 of PCT/6B9B/00068 filed Jan. 14, 1993, now U.S. Pat. No. 5,578,591.

This invention relates to novel β-lactam compounds, their preparation and their use, and in particular to a novel class of 2-isocephems. These compounds have antibacterial properties, and are therefore of use in the treatment of bacterial infections in humans and animals caused by a wide range of organisms.

J. Med. Chem. (1988), 31, 1190–1196 discloses 0-2-isocephems of general formula (A):

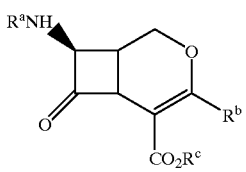

(A)

wherein $R^a$, $R^b$ and $R^c$ are various substituents.

We have found a particularly advantageous class of 2-isocephems bearing a cyclic ether or thio-ether substituent at the 3-position of the cephem nucleus.

The present invention provides a compound of formula (I) or a salt thereof:

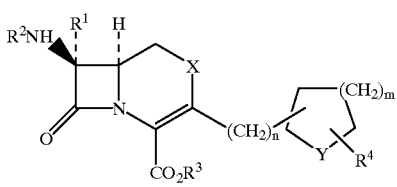

(I)

wherein
- $R^1$ is hydrogen, methoxy or formamido;
- $R^2$ is an acyl group, in particular that of an antibacterially active cephalosporin;
- $CO_2R^3$ is a carboxy group or a carboxylate anion, or $R^3$ is a readily removable carboxy protecting group or a pharmaceutically acceptable salt-forming group or in vivo hydrolysable ester group;
- $R^4$ represents hydrogen or up to four substituents, which may be present on any of the carbon atoms in the ring system shown, selected from alkyl, alkenyl, alkynyl, alkoxy, hydroxy, halogen, amino, alkylamino, acylamino, dialkylamino, $CO_2R$, $CONR_2$, $SO_2NR_2$ where R is hydrogen or alkyl, aryl and heterocyclyl, which may be the same or different and wherein any $R^4$ alkyl substituent is optionally substituted by one or more substituents selected from the list from which $R^4$ is selected;
- X is O, S, SO or $SO_2$; Y is O, S, SO or $SO_2$; n is 0 or 1; and m is 1 or 2.

The bonding carbon atom of the cyclic ether or thio-ether moiety which links the ring to the cephem nucleus is generally asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

Since the compounds of the present invention are intended for use as therapeutic agents for antibacterial use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

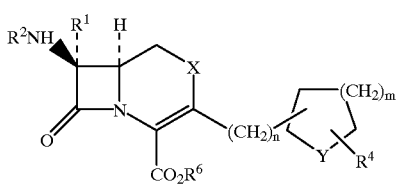

(Ia)

wherein $R^1$, $R^2$, $R^4$, m, n, X and Y are as defined with respect to formula (I) and the group $CO_2R^6$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective amount of an antibiotic compound of the formula (Ia) or a pharmaceutically acceptable in vivo hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

Also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group, an oxime radical of formula $-N=CHR^7$ where $R^7$ is aryl or heterocyclic, or an in vivo hydrolysable ester radical such as defined below.

A carboxyl group may be regenerated from any of the above esters by usual methods appropriate to the particular $R^3$ group, for example, acid and base- catalysed hydrolysis, or by enzymically-catalysed hydrolysis, or by hydrogenolysis under conditions wherein the remainder of the molecule is substantially unaffected.

When used herein the term 'aryl' includes phenyl and naphthyl, each optionally substituted with up to five, preferably up to three, groups selected from halogen, mercapto, $(C_{1-6})$ alkyl, phenyl, $(C_{1-6})$ alkoxy, hydroxy$(C_{1-6})$alkyl, mercapto$(C_{1-6})$alkyl, halo$(C_{1-6})$ alkyl, hydroxy, amino, nitro, carboxy, $(C_{1-6})$alkylcarbonyloxy, $(C_{1-6})$ alkoxycarbonyl, formyl, or $(C_{1-6})$alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$ alkoxy, halo$(C_{1-6})$alkyl, hydroxy, carboxy, carboxy salts, carboxy esters such as $(C_{1-6})$alkoxycarbonyl, $(C_{1-6})$ alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

The term 'heteroaryl' as used herein means a heteroaromatic heterocyclic ring or ring system, suitably having 5 or 6 ring atoms in each ring.

When used herein the terms 'alkyl', 'alkenyl', 'alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

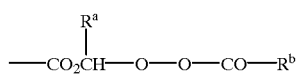

(i)

-continued

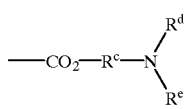

(ii)

(iii)

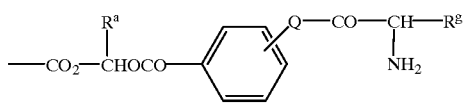

(iv)

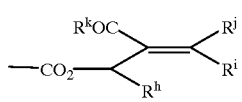

(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$((C_{1-6})$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$((C_{1-6}))$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylamninoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

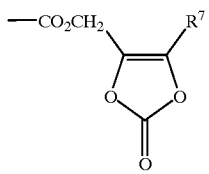

wherein $R^5$ is hydrogen, $(C_{1-6})$ alkyl or phenyl.

A preferred in vivo hydrolysable ester group is the pivaloyloxymethyl ester.

Suitable pharmaceutically acceptable salts of the carboxy group of the compound of formula (I) include metal salts, eg aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylarnine, bis-(2-hydroxyethyl)amine or tris-(2-hydroxyethyl)-amine, cycloalkylamines such as dicyclohexylamine, or with procaine, dibenzylamine, N,N-dibenzylethylene-diamine, 1-ephenamine, N-methylmorpholine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium salt and silver salt. Salts of formula (I) may be prepared by salt exchange in conventional manner.

In compounds of formula (I) or (Ia), each of the groups X and Y may independently be an oxidised sulphur atom, i.e. a sulphoxide (SO) or sulphone ($SO_2$) group. When X and/or Y is/are sulphoxide it will be understood that α- and β-isomers may exist; both such isomers are encompassed within the scope of the present invention.

Preferably X is O or S.

Preferably Y is O or S.

Advantageously, $R^1$ is hydrogen.

Suitably, the cyclic ether or thio-ether at the 3-position of the cephalosporin nucleus is unsubstituted or substituted by up to three substituents $R^4$, selected from ($C_{1-6}$) alkyl, for example methyl, ($C_{1-6}$) alkoxy, for example methoxy, ($C_{1-6}$) alkoxycarbonyl for example methoxycarbonyl, ($C_{1-6}$) alkoxy ($C_{1-6}$) alkyl, for example methoxymethyl, and ($C_{1-6}$) alkanoyloxy ($C_{1-6}$) alkyl, for example acetoxymethyl.

Preferably the cyclic ether or thio-ether at the 3-position of the cephalosporin nucleus is unsubstituted.

Preferably m is 1.

Suitably the cyclic ether at the 3-position of the cephalosporin nucleus is a tetrahydrofuran-2-yl group.

Preferably n is 0.

Preferably the cyclic thio-ether is bonded to the cephalosporin nucleus at a ring carbon adjacent to the oxygen or sulphur heteroatom.

Suitable acyl groups $R^2$ include those of formulae (a)–(f):

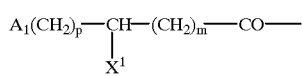

(a)

(b)

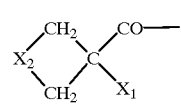

(c)

(d)

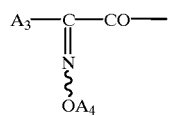

(e)

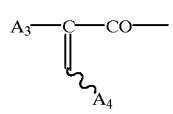

(f)

wherein p is 0, 1 or 2; m is 0, 1 or 2; $A_1$ is ($C_{1-6}$) alkyl, substituted ($C_{1-6}$) alkyl wherein the substituents may be as for $R^4$ above, ($C_{3-6}$) cycloalkyl, cyclohexenyl, cyclohexadienyl, an aryl (including heteroaryl) group, such as phenyl, substituted phenyl, thienyl, pyridyl, or an optionally substituted thiazolyl group, a ($C_{1-6}$) akylthio group or ($C_{1-6}$) alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aryl group, for example a phenyl, 2,6-dimethoxyphenyl, 2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —$CH_2OCH_2$—, —$CH_2SCH_2$— or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, ($C_{1-6}$)alkyl, ($C_{3-8}$) cycloalkyl, ($C_{3-8}$) cycloalkyl($C_{1-6}$)alkyl, ($C_{1-6}$) alkoxycarbonyl($C_{1-6}$) alkyl, ($C_{2-6}$) alkenyl, carboxy($C_{1-6}$)alkyl, ($C_{2-6}$) alkynyl, aryl or ($C_{1-6}$)alkyl substituted by up to three aryl groups.

Suitably when $R^2$ is a group (a), $A_1$ is ($C_{1-6}$) alkyl, ($C_{3-6}$) cycloalkyl, cyclohexenyl, cyclohexadienyl, phenyl, substituted phenyl (eg substituted as for "aryl" above) such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is 0.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino-1,2,4-thiadiazol-3-yl and 4-aminopyrimid-2-yl.

In compounds of formula (Ia) a preferred acyl group $R^2$ is one of formula (e), having a group, $A_3$ which is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Preferably the six-membered oxygen- or sulphur-containing ring of formula (I) and (Ia) has the configuration:

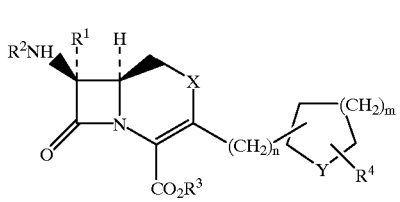

(Ia)

Certain compounds of the invention include an amino group which may be protected. Suitable amino protecting groups are those well known in the art which may be removed under conventional conditions without disruption of the remainder of the molecule.

Examples of amino protecting groups include $(C_{1-6})$ alkanoyl; benzoyl; benzyl optionally substituted in the phenyl ring by one or two substituents selected from $(C_{1-4})$ alkyl, $(C_{1-4})$ alkoxy, trifluoromethyl, halogen, or nitro; $(C_{1-4})$ alkoxycarbonyl; benzyloxycarbonyl or trityl (ie triphenylmethyl) substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85% especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following pharmaceutically acceptable carboxylic acids, salts and in-vivo hydrolysable esters:

Sodium (6S,7S)-7-[2-(2-Aminothiazol-4-yl)-2-(Z)-methoxyiminoacetamido]-3-[(S)-(tetrahydrofuran-2-yl]isoceph-3-em-4-carboxylate, and Sodium (6S,7S)-7-[2-(2-aminothiazol-4-yl)-2-(Z)-methoxyiminoacetamido]-8-oxo-3-(tetrahydrofuran-2-yl)-aza-4-oxabicyclo[4.2.0]oct-2-ene-2-carboxylate.

The present invention provides a process for the preparation of a compound of formula (I) or (Ia) as defined above in whichi $—CO_2R^3$ is a carboxy group or carboxylate anion or $R^3$ is a pharmaceutically acceptable salt-forming group or in-vivo hydrolysable ester group, wherein a compound of formula (I) as defined above in which $R^3$ is a carboxy protecting group has its group $CO_2R^3$ repaced by a group $CO_2R^3$ which is a carboxy group or a carboxylate anion, or in which $R^3$ is a pharmaceutically acceptable salt-forming group or in-vivo hydrolysable ester group.

The present invention further provides a process for the preparation of a compound of formula (I), which process comprises treating a compound of formula (II) or a salt thereof:

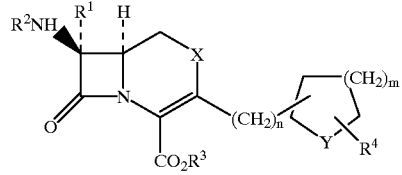

(II)

wherein $R^1$, $CO_2R^3$, $R^4$, m, n, X and Y are as hereinbefore defined, wherein any reactive groups may be protected, and wherein the amino group is optionally substituted with a group which permits acylation to take place; with an acid of formula (III) or a N-acylating derivative thereof:

$R^2OH$ (III)

wherein $R^2$ is the acyl group as defined with respect to formula (I) and wherein any reactive groups may be protected; and thereafter, if necessary or desired, carrying out one or more of the following steps:
  i) removing any protecting groups;
  ii) converting the group $CO_2R^3$ into a different group $CO_2R^3$;
  iii) converting the group $R^2$ into a different group $R^2$;
  iv) converting the group X into a different group X, for example X into SO or $SO_2$;
  v) converting the group Y into a different group Y, for example S into SO or $SO_2$;
  vi) converting the product into a salt or ester.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula $—P.R^7R^8$ wherein $R^7$ is an alkyl, haloalkyl, aryl, aralkyl, alkoxy, haloalkyl, aryl, aralkyl, alkoxy, haloalkoxy, aryloxy, aralkyloxy or dialkylamino group, $R^8$ is the same as $R^7$ or is halogen or $R^7$ and $R^8$ together form a ring; suitable such phosphorus groups being $—P(OC_2H_5)_2$, $—P(C_2H_5)_2$,

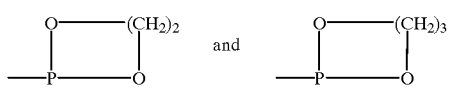

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl)acetamide, N,O-bis (trimethylsilyl)-trifluoroacetamide, N-methyl-N-trimethylsilylacetamide, N-methyl-N-trimethylsilyl-trifluroacetamide, N,N'-bis(trimethylsilyl)urea, and N,O-bis (trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30–60° C., preferably 40–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (eg chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexyl-carbodiimide, or N-ethyl-N'-[3-(dimethylamino)propyl]-carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3-C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

The optional removal of protecting group (i), the optional conversion of $CO_2R^3$ (ii), the optional conversion (iii) of $R^2$ to a different $R^2$, $CO_2R^3$ to a different $CO_2R^3$, (iv) X to a different X, (v) Y to a different Y, and (vi) the optional formation of a salt or ester, may be carried out using methods well known in the art of cephalosporin and penicillin chemistry.

For example, when the group X or Y is S, SO, or $SO_2$, the group X or Y may be converted into a different group Y by methods of oxidation or reduction well known in the art of cephalosporin and penicillin synthesis, as described, for example, in EP-A-0 114 752. For example, sulphoxides (in which X or Y is SO) may be prepared from the corresponding sulphide (in which X or Y is S) by oxidation with a suitable oxidising agent, for example an organic peracid such as m-chloroperbenzoic acid.

A reduction step is generally effected by processes well known in the art of β-lactam chemistry, for example using phosphorus trichloride in dimethylformamide.

For example, removal of protecting groups may be carried out by any convenient method known in the art such that unwanted side reactions are minimised. When for example $R^3$ is the protecting group p-methoxybenzyl, this group may suitably be removed by treatment of the protected compound with aluminium chloride in the presence of anisole. Separation of unwanted by-products may be carried out using standard methods.

In a further process of the invention, compounds of formula (I) and (II) wherein X is S, SO or $SO_2$ may be prepared by cyclising a compound of formula (IX):

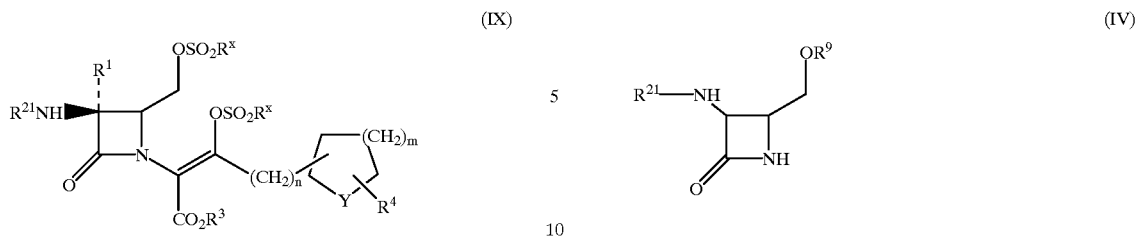

(IX)

wherein Y, $R^1$, $R^4$, and m, n, and $CO_2R^3$ are as hereinbefore defined; each $R^x$ may be the same or different and is independently selected from ($C_{1-6}$) alkyl or aryl; and $R^{21}$ is a group $R^2$ as hereinbefore defined or is an amino-protecting group or is a group which permits acylation to take place, and thereafter if necessary or desired, carrying out one or more of the following steps:

i) removing any protecting groups;
ii) converting the group $CO_2R^3$ into a different group $CO_2R^3$;
iii) converting the group $R^{21}$ into a different group $R^{21}$;
iv) converting the group Y into a different group Y;
v) converting the product into a salt.

When in the compound of formula (IX) $R^{21}$ is a group which permits acylation to take place, for example either by displacement or after removal to form the parent amino group the compound which is formed as a result of the cyclisation is a compound of formula (II).

Each $R^x$ is preferably methyl.

The cyclisation of the compound of formula (IX) may be achieved by treatment of the compound with a reducing agent such as sodium hydrogen sulphide for example in a solvent such as dimethyl sulphoxide.

Compounds of formula (IX) may for example be prepared from compounds of formula (VIII):

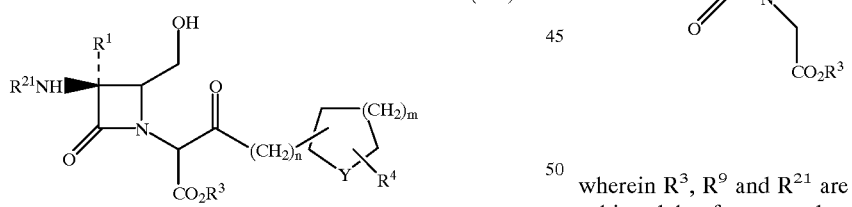

(VIII)

wherein Y, $R^1$, $R^4$, $R^{21}$, m, n, and $CO_2R^3$ are as hereinbefore defined, by reaction of an acid of formula $R^x.SO_2.OH$ or an acylating derivative thereof wherein $R^x$ is as hereinbefore defined. Suitable acylating derivatives include the types of derivatives from which N-acylating derivatives of the acid of formula (III) above are selected. Preferred acylating derivatives are halides of the formula $R^x.SO_2.Cl$, for example methane sulphonyl chloride. The reaction may be carried out in the presence of an acid binding agent, such as those described above for the N-acylation, especially tertiary amines such as triethylamine.

Compounds of formula (VIII) may be prepared from known azetidinone starting compounds of formula (IV):

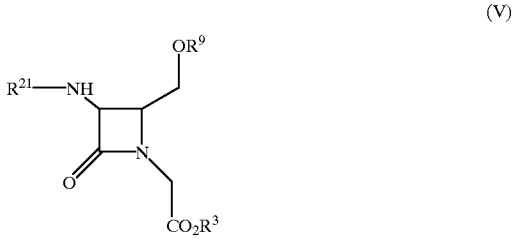

(IV)

wherein $R^{21}$ is an amino protecting group such as those described above, for example trityl, and $R^9$ is a hydroxy protecting group.

A hydroxy-protecting group $R^9$ may be a conventional protecting group such as an alkanoic ester group such as a ($C_{1-4}$) alkoxy carbonyl group such as tert-butyloxycarbonyl, a ($C_{1-4}$) halogenoalkoxycarbonyl group such as 2-iodoethyloxycarbonyl or 2,2,2-trichloro-ethyloxycarbonyl, an aralkyloxycarbonyl group such as benzyloxycarbonyl, a tri($C_{1-4}$)alkylsilyl group such as tert-butyldimethylsilyl or trimethylsilyl, a ($C_{4-10}$) tert-alkyl group such as tert-butyl and a substituted or unsubstituted mono-, di or tri-phenylmethyl group such as benzyl, p-methoxybenzyl, diphenylmethyl, di(p-anisyl)methyl or trityl. The preparation of such compounds is for example described in Mastalerz et al, J. Med. Chem, (1988), 31, 1190–1196, see in particular compound (9) on P1193 thereof.

Compounds of formula (IV) may be N-substituted to form compounds of formula (V):

(V)

$$\text{R}^{21}\text{—NH} \diagdown \overset{\overset{\displaystyle OR^9}{|}}{\underset{\underset{\displaystyle CO_2R^3}{|}}{\underset{O}{\diagup}}}$$

wherein $R^3$, $R^9$ and $R^{21}$ are as defined above. This may be achieved by for example treatment of the compound of formula (IV) with a compound of formula $Z—CH_2—CO_2R^3$ in which Z is a halogen, in particular chlorine, bromide or iodine, and $R^3$ is as defined in formula (I), in particular being a readily removeable carboxy protecting group, such as p-methoxybenzyl, in the presence of caesium carbonate. Suitable conditions for this procedure are described for example in Murakamni et al, J. Antibiotics (1990) 43 1441–49. An alternative method of N-substitution is described in Mastalerz op cit, eg on P1193, in which compounds of formula (V) having other $R^3$ groups may be formed.

Compounds of formula (V) may be converted into compounds of formula (VI):

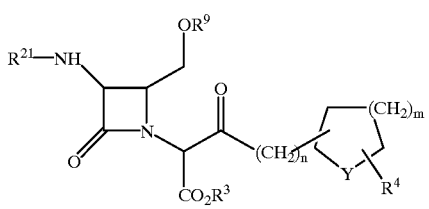

(VI)

wherein $R^3$, $R^4$, $R^9$, $R^{21}$, Y and m and n are as defined above. This may be achieved by example treating the compound of formula (V) firstly with lithium bis(trimethylsilyl)amide, then after reaction, with a compound of formula (VII):

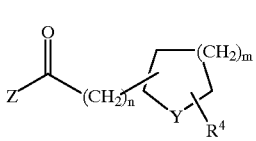

(VII)

wherein $R^4$, Y, m and n are as defined above, and Z is a halogen, in particular chlorine. Compounds of formula (VII) are known, for example tetrahydrofuroyl chloride. Suitable conditions for this procedure are for example described in Mastalerz op cit, eg on P1193.

Compounds of formula (VI) may be converted into compounds of formula (VIII) by removal of the hydroxy protecting group $R^9$ to form an OH group. Such protecting group $R^9$ may be removed by conventional methods appropriate to the $R^9$ group concerned. Form example if $R^9$ is a tert-butyl dimethylsilyl group, the OH group may be formed by treatment with tetrabutylammonium fluoride in a THF solvent. Suitable conditions for this deprotection step are for example described in Mastalerz op cit.

Compounds of formula (I) and (II) in which X is O may be prepared by cyclising a compound of formula (VIII) as described above then thereafter if necesssary or desired, comprising out one or more of the following steps:

i) removing any protecting groups;
ii) converting the group $CO_2R^3$ into a different group $CO_2R^3$;
iii) converting the group $R^{21}$ into a different group $R^{21}$;
iv) converting the group Y into a different group Y;
v) converting the product into a salt.

The reaction by which the compound of formula (VIII) is cyclised is an intramolecular reaction and is typically carried out under the conditions of the Mitsunobu reaction (eg Mitsunobu, O "Synthesis" 1981, 1) eg by treatment with a trialkyl or triaryl phosphorous compound, for example a ($C_{1-6}$) trialkylphosphene such as tri-n-butylphosphene, or triphenylphosphene, in the presence of a dialkyl azodicarboxylate, e.g. diethyl or diisopropyl azodicarboxylate.

Starting from a compound of formula (IV) as described above results in a compound of formula (I) in which $R^2$ is the group $R^{21}$, ie an amino protecting group. Where $R^2$ in a compound of formula (I) is required to be different from the group $R^{21}$ in the compound of formula (IV), the conversion may be effected via the intermediacy of a compound of formula (II) which has an amino group at the 7-position of the cephem nucleus.

An $R^{21}$ acyl side-chain may be removed by the Delft procedure commonly used in β-lactam chemistry. Suitable reaction conditions include treatment with phosphorus pentachloride and N-methylmorpholine at reduced temperature. When $R^{21}$ is a trityl group, this may suitably be removed by treatment of the compound with paratoluenesulphonic acid in a solvent such as methanol. These procedures yield the compound of formula (II), which may then be treated with the acid (III) or its derivative.

Compounds of formula (II), (VI), (VIII) and (IX) are believed to be novel compounds and as such form part of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (X) or a pharmaceutically acceptable salt or ester thereof:

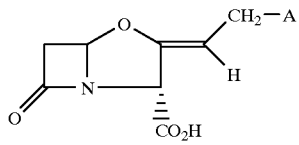

(X)

wherein

A is hydroxyl, substituted hydroxyl, thiol, substituted thiol, amino, monoor di-hydrocarbyl-substituted amino, or mono- or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (XI) or a pharmaceutically acceptable salt or in vivo hydrolysable ester thereof:

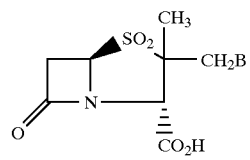

(XI)

wherein
B represents hydrogen, halogen or a group of formula:

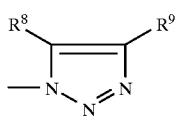

in which $R^8$ and $R^9$ are the same or different and each represents hydrogen, $(C_{1-6})$ alkoxycarbonyl or carboxy, or a pharmaceutically acceptable salt thereof.

Further suitable β-lactamase inhibitors include 6-alkylidene penems of formula (XII):

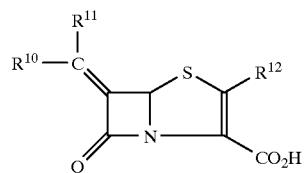

(XII)

or a pharmaceutically acceptable salt or in vivo hydrolysable ester thereof, wherein $R^{10}$ and $R^{11}$ are the same or different and each represents hydrogen, or a $(C_{1-10})$ hydrocarbon or heterocyclic group optionally substituted with a functional group; and $R^{12}$ represents hydrogen or a group of formula $R^{13}$ or —$SR^{13}$ where $R^{13}$ is an optionally substituted $(C_{1-10})$ hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolyzable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as *E. coli* and Gram-positive organisms such as *S. aureus*.

The following Examples illustrate the preparation of compounds of the invention and intermediates thereto.

EXAMPLE 1

Sodium (6S,7S)-7-[2-(2-Aminothiazol-4-yl)-2-(Z)-methoxyiminoacetamido]-3-[(S)-tetrahydrofuran-2-yl]isoceph-3-em-4-carboxylate a) 4-Methoxybenzyl 2-[(3S,4S)-4-t-Butyldimethylsilyloxymethyl-2-oxo-3-tritylaminoazetidin-1-yl]acetate (V)

(3S,4S)-4-t-Butyldimethylsilyloxymethyl-3-tritylaminoazetidinone (IV), (1.67 g) [H. Mastalerz et al., J. Med. Chem., 1988, 31, 1190] as a suspension in acetonitrile (40 ml) was treated with DMF (20 ml) to obtain a clear solution. Cesium carbonate (1.29 g) followed by 4-methoxybenzyl bromoacetate (1.19 g) were added and the mixture vigorously stirred overnight. T.l.c. analysis showed no starting material, the solution was diluted with ethyl acetate and washed with water (4×), brine and then dried. Removal of solvent in vacuo and purification by flash chromatography afforded the title compound as a pale yellow foam, (1.744 g, 76%), $v_{max}$ ($CH_2Cl_2$) 1760 and 1744 $cm^{-1}$; $\delta_H$ ($CDCl_3$) −0.06 and −0.13 (6H, 2s), 0.81 (9H, s), 1.60 (1H, brs), 2.44 (1H, dd, J 3.3, 11.7 Hz), 3.10 (1H, dd, 2.2, 11.7 Hz), 3.29 (1H, m), 3.41 (1H, d, J 18.0 Hz), 3.80 (3H, s), 4.36 (1H, d, J 18.0 Hz), 4.45 (1H, m), 4.97 and 5.05 (2H, ABq, J 11.8 Hz), 6.85 (2H, d, J 8.7 Hz), 7.16–7.30 (15H, m) and 7.52 (2H, d, J 8.7 Hz); [mass spectrum: $MH^+$ (651)].

(b) 4-Methoxybenzyl 2-[(3S,4S)-4-t-Butyldimethylsilyloxymethyl-2-oxo-3-tritylaminoazetidin-1-yl]-3-oxo-3-(S-tetrahydrofuran-2-yl)propionate (VI)

2'-S-Tetrahydrofuroic acid (VII) in dichloromethane (10 ml) was treated with oxalyl chloride (0.674 g, 0.463 ml) and 1 drop of DMF at room temperature for 1 ½ h. The solvent was removed in vacuo and the residue re-evaporated (2×) from dichloromethane. The crude acid chloride ((VII) derivative) was then dissolved in dry THF (3 ml) for the next stage. The azetidinone (IV) from example 1(a), (1.725 g) in dry THF (25 ml) under argon was cooled to −78° C. and treated with lithium bis(trimethylsilyl)amide (5.44 ml, 1M solution in THF) and the red solution stirred for 3 min. The acid chloride solution was added in one portion, stirred at −78° C. for 35 min. then quenched with acetic acid (0.525 g, 0.496 ml to to give a yellow solution. The reaction mixture was allowed to warm to room temperature and then partitioned between ethyl acetate and water. The organic phase was washed with water (2×), brine and then dried. Concentration afforded a pale yellow foam. Flash chromatography on silica gel, eluting with 30, 40 and then 50% ethyl acetate/hexane gave the title compound as a pale yellow foam, (1.5 g, 76%); $v_{max}$ ($CH_2Cl_2$) 3351 (w) and 1763 (br)$cm^{-1}$; [mass spectrum: $MH^+$ (749)].

(c) 4-Methoxybenzyl 2-[(3S,4S)-4-Methanesulphonyloxymethyl-2-oxo-3-tritylaminoazetidin-1-yl]-3-methanesulphonyloxy-3-(S-tetrahydrofuran-2-yl)propenoate (IX)

The azetidinone (VI) from example 1(b), (1.866 g) in dry THF (30 ml) at room temperature, was treated with tetrabutylammonium fluoride (3 ml, 1M solution in THF) for 20 min., and then quenched with excess acetic acid (0.5 ml) to form the de-protected hydroxy compound (VIII). The solution was diluted with ethyl acetate, washed with water (3×), brine and then dried.

After removal of solvent, the residue was dissolved in dichloromethane (30 ml), cooled in ice/water and treated with triethylamine (0.765 ml) and methanesulphonyl chloride (0.43 ml). The solution was stirred at room temperature for 30 min. T.l.c. (50% ethyl acetate/hexane) showed no starting material. Column chromatography on silica gel, eluting with 50% ethyl acetate/hexane afforded the title compound (IX) as a colourless foam (0.777 g, 39%); $v_{max}$ ($CH_2Cl_2$) 1776, 1729 and 1614 $cm^{-1}$; $\delta_H$ ($CDCl_3$) 1.80–2.09 (4H, m), 2.79 (3H, s), 2.94 (1H, d, J 7.4 Hz), 3.26 (4H, s and m), 3.74–4.05 (7H, s and m), 4.46 (1H, dd, J 5.0, 7.4 Hz), 5.10 (1H, m), 5.08 and 5.24 (2H, ABq, J 11.9 Hz), 6.88 (2H, d, J 8.6 Hz) and 7.21–7.40 (17H, m); [mass spectrum: +ve ion (3NOBA, $Na^+$), $MNa^+$ (813)].

(d) 4-Methoxybenzyl (6S,7S)-3-[(S)-Tetrahydrofuran-2-yl]-7-tritylaminoisoceph-3-em-4-carboxylate ((II) protected)

The azetidinone (IX) from example 1(c), (0.777 g) in dry DMSO (2 ml) was treated with excess sodium hydrogen sulphide in portions as a solid until the solution remained green and t.l.c. analysis showed complete loss of starting material (60% ethyl acetate/hexane). The reaction mixture was diluted with ethyl acetate, washed with water (3×), brine and dried. Concentration afforded a colourless foam. Flash chromatography on silica gel, eluting with 20, 30% ethyl acetate/hexane gave the title compound as a colourless foam, (0.632 g, 100%); $v_{max}$ ($CH_2Cl_2$) 1766, 1707 and 1613 $cm^{-1}$; $\delta_H$ ($CDCl_3$) 1.30 (1H, dd, J 3.1, 12.4 Hz), 1.65–1.97 (3H, m), 2.27–2.37 (1H, m), 2.53 (1H, dd, J 10.1, 12.4 Hz), 2.75 (1H, br s), 3.13–3.20 (1H, m), 3.73–3.94 (5H, m and s), 4.75 (1H, d, J 4.4 Hz), 5.06 (1H, m), 5.09 and 5.20 (2H, ABq, J 12.4 Hz), 6.87 (2H, d, J 8.7 Hz) and 7.21–7.43 (17H, m); [mass spectrum: +ve ion (3NOBA, $Na^+$) $MNa^+$ (655)].

(e) 4-Methoxybenzyl (6S,7S)-3-Amino-7-(S)-tetrahydrofuran-2-ylisoceph-3-em-4-carboxylate (II)

The isocephem from example 1(d), (0.653 g) in dichloromethane (5 ml) was cooled in ice/water and treated with a solution of 4-toluenesulphonic acid (0.236 g) in methanol (2.5 ml). Left to stir in ice/water for 24 h. The solution was partitioned between ethyl acetate and sat. sodium hydrogen carbonate. The organic phase was washed with water, brine and then dried. Concentration afforded a colourless solid. Flash chromatography on silica gel, eluting with ethyl acetate and then 5% methanol/ethyl acetate gave the title compound as a colourless crystalline solid, (0.281 g, 70%); (Found: $M^+$, 390.1249. $C_{19}H_{22}N_2O_5S$ requires M, 390.1249); $v_{max}$ ($CH_2Cl_2$) 1766 and 1708 $cm^{-1}$; $\delta_H$ ($CDCl_3$) 1.74–2.03 (3H, m), 2.34–2.44 (1H, m), 2.85 (1H, dd, J 10.1, 12.5 Hz), 3.01 (1H, dd, J 3.3, 12.5 Hz), 3.81 (5H, m), 3.94–4.03 (1H, m), 4.66 (1H, d, J 5.1 Hz), 5.12 (1H, m), 5.16 (3H, s), 6.88 (2H, d, J 8.7 Hz) and 7.35 (2H, d, J 8.7 Hz).

(f) 4-Methoxybenzyl (6S,7S)-7-[2-(2-Aminothiazol-4-yl)-2-(Z)-methoxyiminoacetamido]-3-[(S)-tetrahydrofuran-2-yl]isoceph-3-em-4-carboxylate (I)

2-(2-Aminothiazol-4-yl)-2-(Z)-methoxyiminoacetic acid (III) (0.155 g) in dry DMF (1 ml), under argon was cooled to −50° C. and treated with diisopropylethylamine (0.099 g, 0.134 ml) followed by methanesulphonyl chloride (0.088 g, 0.06 ml). The temperature was maintained between −50 and −40° C. for 30 min. The isocephem (II) from example 1(e), (0.273 g) in dry DMF (1 ml) and pyridine (0.055 g, 0.057 ml) was added and the reaction mixture allowed to warm to room temperature over 2 h. The solution was diluted with ethyl acetate, washed with sat. sodium hydrogen carbonate, water (2×), brine and then dried. The solvent was removed in vacuo. Flash chromatography on silica gel, eluting with 80% ethyl acetate/hexane and then ethyl acetate afforded the title compound as a colourless solid, (0.379g, 95%); $v_{max}$ ($CH_2Cl_2$) 3477, 3305, 3205, 1761, 1709, 1677 and 1614 $cm^{-1}$; $\delta_H$ ($CDCl_3$) 1.76–2.05 (3H, m), 2.32–2.42 (1 H, m), 3.01–3.14 (2H, m), 3.82 (4H, s and m), 3.96 (4H, s and m), 4.05–4.14 (1H, m), 5.13 (1H, m), 5.17 (2H, s), 5.79 (1H, dd, J 4.7, 7.5 Hz collapses to d, J 4.7 Hz with $D_2O$), 5.86 (2H, br s, exchangeable with $D_2O$), 6.64 (1H, s), 6.89 (2H, d, J 8.7 Hz), 7.33 (2H, d, J 8.7 Hz) and 8.80 (1H, d, J 7.5 Hz exchangeable with $D_2O$); [mass spectrum: +ve ion (thioglycerol) $MH^+$ (574)].

(g) Sodium (6S,7S)-7-[2-(2-Aminothiazol-4-yl)-2-(Z)-methoxyiminoacetamido]-3-[(S)-tetrahydrofuran-2-yl]isoceph-3-em-4-carboxylate (I)

A mixture of dichloromethane (5 ml) and anisole (5 ml), under argon was cooled to −20° C. and aluminium trichloride (0.253 g) added. After 15 min. the solution was cooled to −40° C. and a solution of the isocephem from example 1(b), (0.363 g) in dichloromethane (2 ml) was added. After 5 min. trisodium citrate (15 ml, 0.5M solution) was added and the reaction mixture warmed to room temperature for 10 min. The aqueous phase was separated and washed with dichloromethane (2×) and concentrated. The concentrated solution was purified by column chromatography on HP20SS resin eluting with 100 ml portions of 0, 1, 2 and 4% THF/water. The fractions containing the product by h.p.l.c. were combined, concentrated and freeze-dried to give the title compound as an amorphous white solid, (0.149 g, 52%); $v_{max}$ (KBr) 1751, 1662,1603 and 1532 cm$^{-1}$; $\delta_H$[(CD$_3$)$_2$SO] 1.62–1.87 (3H, m) 2.14–2.21 (1H, m), 2.75–2.88 (2 H, m), 3.59–3.67 (1H, m), 3.72–3.78 (1H, m), 3.84 (4H, m and s), 5.09 (1H, t, J 6.7 Hz), 5.43 (1H, dd, J 4.9, 8.9 Hz, collapses to d, J 4.9 Hz with D$_2$O), 6.79 (1H, s), 7.24 (2H, s, exchangeable with D$_2$O) and 9.13 (1H, d, J 8.9 Hz, exchangeable with D$_2$O); [mass spectrum: +ve ion (glycerol) MH$^+$ (454)].

EXAMPLE 2

Sodium (6S,7S)-7-[2-(2-Aminothiazol-4-yl)-2-(Z)-methoxyiminoacetamido]-8-oxo-3-3-(tetrahydrofuran-2-yl)-1-aza-4-oxabicyclo[4.2.0]oct-2-ene-2-carboxylate (a) 4-Methoxybenzyl 2-[(3S,4S )-4-t-Butyldimethylsilyloxymethyl-2-oxo-3-tritylaminoazetidin-1-yl]acetate (V)

Cesium carbonate (1.58 g) was added to a stirred solution of (3S,4S)-4-t-butyldimethylsilyloxymethyl-3-tritylaminoazetidin-2-one (1.45 g) (IV) (H. Mastalerz et al., J. Med. Chem., 1988, 31, 1190–1196) in a mixture of acetonitrile (44 ml) and dimethylformamide (35 ml). 4-Methoxybenzyl bromoacetate (1.44 g) was then added and the mixture stirred at room temperature for 48 h. The mixture was then partitioned between ethyl acetate and water, the organic phase was washed four times with water, and then with brine. The solution was dried over magnesium sulphate and evaporated. The title compound (2.29 g) was isolated by column chromatography of the residue (Silica gel, 3:1 hexane:ethyl acetate as eluent). [α]$_D^{21}$ −9.0°; $v_{max}$ (CHCl$_3$) 3352, and 1755 cm$^{-1}$; δ(CDCl$_3$) −0.04 (3H, s), 0.00 (3H, s), 0.88 (9H, s), 1.69 (1H, br s), 2.54 (1H, dd, J 3.33 and 11.68 Hz), 3.19 (1H, dd, J 2.05 and 11.68 Hz), 3.38 (1H, m), 3.51 (1H, d, J 17.98 Hz), 3.90 (3H, s), 4.46 (1H, d, J 17.98 Hz), 4.54 (1H, m), 5.06 (1H, d, J 11.79 Hz), 5.15 (1H, d, J 11.81 Hz), 6.94 (2H, d, J 8.68 Hz), 7.2–7.65 (17H, m).

(b) 4-Methoxybenzyl 2-[(2S,4S)-4-t-Butyldimethylsilyloxymethyl-2-oxo-3-tritylaminoazetidin-1-yl]-2-(tetrahydrofuran-2-ylcarbonyl)acetate (VI)

Oxalyl chloride (0.47 ml) was added to a stirred solution of (S)-tetrahydrofuroic acid (0.448 g) in dichloromethane (9 ml). Dimethylformamide (1 drop) was added and the mixture was stirred at room temperature for 1 h, and then heated to reflux for 15 min. The mixture was cooled and and the solvent evaporated and chloroform was evaporated from the residue containing the acid chloride (VIII) twice. A solution of 4-methoxybenzyl 2-[(3S,4S)-4-t-butyldimethylsilyloxymethyl-2-oxo-3-tritylaminoazetidin-1-yl]acetate (V) (2.29 g) in tetrahydrofuran (40 ml) was cooled to −78° C., and a solution of lithium bis(trimethylsilyl)amide (8 ml of a 1N solution in tetrahydrofuran) was added. The mixture was stirred at −78° C. for 3 min. and then a solution of the previously prepared acid chloride in tetrahydrofuran (4 ml) was added. The mixture was stirred for a further 35 min. at −78° C. and then acetic acid (0.8 ml) was added. The mixture was allowed to warm to room temperature and then partitioned between ethyl acetate and water. The organic phase was washed twice with water, then with brine, dried over magnesium sulphate and evaporated. Column chromatography of the residue using gradient elution (silica gel, 1:1 hexane:ethyl acetate going to neat ethyl acetate) gave the title compound (1.41 g) as a mixture of isomers. $v_{max}$ (CHCl$_3$) 1761 and 1746 cm$^{-1}$.

(c) 4-Methoxybenzyl (6S,7S)-8-Oxo-3-(tetrahydrofuran-2-yl)-7-(tritylamino)-1-aza-4-oxabicyclo[4.2.0]oct-2-ene-2-carboxylate ((II) amino-protected)

Tetrabutylammonium fluoride (2.75 ml of a 1N solution in tetrahydrofuran) was added to a stirred solution of 4-methoxybenzyl 2[(3S,4S)-4-t-butyldimethylsilyloxymethyl-2-oxo-3-tritylaminoazetidin-1-yl]-2-(tetrahydrofuran-2-ylcarbonyl)acetate (VI) (1.41 g) in tetrahydrofuran (30 ml). The mixture was stirred for 15 min. and then acetic acid (0.19 ml) was added. The mixture was partitioned between ethyl acetate and water and the organic phase was washed twice with water, then brine, dried over magnesium sulphate and evaporatedto yield the hydroxy compound (VIII). The residue was dissolved in tetrahydrofuran (35 ml) and triphenylphosphine (517 mg) was dissolved in the stirred solution. Diethylazodicarboxylate (0.313 ml ) was added and the mixture stirred at room temperature for 15 min., and then the solvent was evaporated. Column chromatography of the residue using gradient elution (silica gel, 3:1 going to 1:1 hexane:ethyl acetate) gave the title compound (II) (927 mg). [α]$_D^{20}$ +44.9°, $v_{max}$ (CHCl$_3$) 1770 and 1708 cm$^{-1}$; δ(CDCl$_3$) 1.66–1.96 (3H, m), 2.10–2.22 (1H, m), 2.79(1H, br s), 3.00–3.12 (2H, m), 3.54 (1H, dd, J 9.07 and 10.03 Hz), 3.72–3.92 (2H, m), 3.80 (3H, s), 4.79 (1H, br s), 5.16 (2H, s), 5.28 (1H, t, J 6.98 Hz), 6.88 (2H, d, J 8.69 Hz), 7.2–7.4 (17H, m).

(d) 4-Methoxybenzyl (6S,7S)-7-Amino-8-oxo-3-(tetrahydrofuran-2-yl)-1-aza-4-oxabicyclo[4.2.0]oct-2-ene-2-carboxylate (II)

A solution of 4-methoxybenzyl (6S,7S)-8-oxo-3-(tetrahydrofuran-2-yl)-7-(tritylamino)-1-aza-4-oxabicyclo[4.2.0]oct-2-ene-2-carboxylate (II) (927 mg) in dichloromethane (7.5 ml) was cooled in an ice bath and a solution of p-toluenesulphonic acid monohydrate (343 mg) in methanol (3.5 ml) was added. The mixture was kept at 0° C. for 17 h and then partitioned between ethyl acetate and sodium bicarbonate solution. The organic phase was washed twice with water, then brine, dried over magnesium sulphate and evaporated. Column chromatography of the residue using gradient elution (silica gel, ethyl acetate going go 5% methanol in ethyl acetate) gave the title compound (II) (418 mg), m.p. 129–131° (from ethyl acetate-hexane), [α]$_D^{20}$ +40.7°; $v_{max}$ (CHCl$_3$) 1771 and 1707 cm$^{-1}$; δ(CDCl$_3$) 1.7–2.1 (5H, m), 2.15–2.3 (1H, m), 3.69–4.01 (3H, m), 3.80 (3H, s,) 4.70 (1H, dd, J 3.53 and 10.63 Hz), 4.77 (1H, d, J 4.97 Hz), 5.14 (1H, d, J 12.01 Hz), 5.20 (1H, d, J 12.05 Hz), 5.35 (1H, t, J 7.24 Hz), 6.88 (1H, d, J 8.69 Hz), 7.36 (1H, d, J 8.67 Hz). (Found C, 60.85; H, 5.75; N, 7.58. C$_{19}$H$_{22}$N$_2$O$_6$ requires: C, 60.95; H, 5.92; N, 7.48).

(e) 4-Methoxybenzyl (6S,7S)-7-[2-(2-Amino thiazol-4-yl)-2-(Z)-methoxyiminoacetamido]-8-oxo-3-(tetrahydrofuran-2-yl)-1aza-4-oxabicyclo[4.2.0]oct-2-ene-2-carboxylate (I)

A stirred mixture of 2-(Z)-methoxyimino-2-(2-aminothiazol-4-yl)acetic acid (III) (54 mg) and N,N- diisopropylethylamine (0.047 ml) in dimethylformamide (0.3 ml) was cooled to −55° to −60° C. and methanesulphonyl chloride (0.021 ml) was added. The mixture was stirred at the same temperature for 0.5 h and then a solution of 4-methoxybenzyl (6S,7S)-7-amino-8-oxo-3-(tetrahydrofuran-2-yl)-1-aza-4-oxabicyclo[4.2.0]oct-2-ene-2-carboxylate (II) (91 mg) in dimethylformamide (1 ml) was added, followed by pyridine (0.022 ml). The mixture was then stirred at 0° C. for 1 h and then at room temperature for 0.5 h. The mixture was partitioned between ethyl acetate and aqueous citric acid solution and the organic phase was washed twice with water, then brine, dried over magnesium sulphate and evaporated. Column chromatography (silica gel, ethyl acetate as eluent) gave the title compound (88 mg). $v_{max}$ (CHCl$_3$) 1769, 1709, 1679 and 1613 cm$^{-1}$; δ(CDCl$_3$) 1.72–2.12 (4H, m), 3.35 (3H, s), 3.68–3.96 (4H, m), 3.76 (3H, s), 4.64 (1H, dd, J 9.19 and 15.89 Hz), 5.13 (3H, s), 5.20 (1H, t, J 6.77 Hz), 5.72 (1H, dd, J 4.14 and 8.91 Hz), 6.80 (1 H, s), 6.93 (2H, d, J 8.68 Hz), 7.24 (2H, s), 7.37 (2H, d, J 8.66 Hz), 9.23 (1H, d, J 9 Hz).

(f) Sodium (6S,7S)-7-[2-(2-Aminothiazol-4-yl)-2-(Z)-methoxyiminoacetamido]-8-oxo-3-(tetrahydrofuran-2-yl)-1-aza-4-oxabicyclo[4.2.0]oct-2-ene-2-carboxylate (I)

A stirred mixture of anisole (2.38 ml) and dichloromethane (1.2 ml) under argon was cooled to −20° C. and treated with aluminium chloride (61 mg). The mixture was stirred at −20° C. for 15 min. and then a slurry of 4-methoxybenzyl (6S,7S)-7-[2-(2-aminothiazol-4-yl)-2-(Z)-methoxyiminoacetamido]-8-oxo-3-(tetrahydrofuran-2-yl)-1-aza-4-oxabicyclo[4.2.0]oct-2-ene-2-carboxylate (I) (88 mg) in dichloromethane (7.5 ml) was added. The mixture was stirred for 5 min. and then trisodium citrate (5.2 ml of 0.5M) was added and the mixture stirred for 10 min. The aqueous phase was separated and washed twice with dichloromethane, then evaporated. The product was purified by HP20SS chromatography of the residue (water with increasing proportions of acetone as eluent). Fractions containing product were combined and evaporated and the residue dissolved in water (4 ml) and freeze-dried to give the title compound (27 mg). $v_{max}$ (KBr) 1757, 1662 and 1617 cm$^{-1}$; δ[(CD$_3$)$_2$SO] 1.68–1.95 (4H, m), 3.58–3.77 (4H, m), 3.84 (3H, s), 4.35 (1H, m), 5.51 (1H, dd, J 3.91 and 8.83 Hz), 5.68 (1H, t, J 6.84), 6.78 (1H, s), 7.25 (2H, s), 9.91 (1H, d, J 8.83 Hz).

We claim:

1. A process for the preparation of a compound of formula (I) or (Ia)

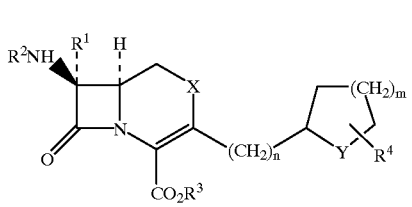
(I)

wherein $R^1$ is hydrogen, methoxy or formamido;

$R^2$ is an acyl group of the formula (a) to (f):

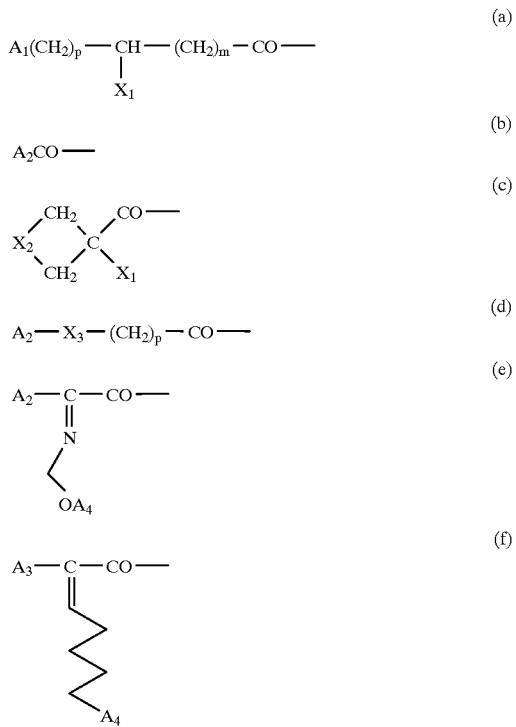

wherein p is 0, 1 or 2; m is 0, 1 or 2; $A_1$ is (C$_{1-6}$)alkyl, substituted (C$_{1-6}$)alkyl wherein the substituents are selected from the list form which $R^4$ is selected, (C$_{3-6}$)cycloalkyl, cyclohexenyl, cyclohexadienyl, phenyl, substituted phenyl, thienyl, pyridyl, or an optionally substituted thiazolyl group, a (C$_{1-6}$)akylthio group or (C$_{1-6}$)alkyloxy; $X_1$ is a hydrogen or halogen atom, a carboxylic acid, carboxylic ester, sulphonic acid, azido, tetrazolyl, hydroxy, amino, ureido, heterocyclylamino, or guanidino; $A_2$ is an aryl group, a substituted C$_{1-6}$alkyl group; or a substituted dithietane; $X_2$ is a —CH$_2$OCH$_2$—, —CH$_2$SCH$_2$— or C$_{2-6}$alkylene group; $X_3$ is an oxygen or sulphur atom; $A_3$ is an aryl or heteroaryl group; and $A_4$ is hydrogen, (C$_{1-6}$)alkyl, (C$_{3-8}$)cycloalkyl, (C$_{3-8}$) cycloalkyl(C$_{1-6}$)alkyl, (C$_{1-6}$)alkoxycarbonyl(C$_{1-6}$) alkyl, (C$_{2-6}$)alkenyl, carboxy(C$_{1-6}$)alkyl, (C$_{2-6}$)akynyl, aryl or (C$_{1-6}$)alkyl substituted by up to three aryl group; wherein said substituent is R$_4$ as defined below;

CO$_2$R$^3$ is a carboxy group or a carboxylate anion, or R$^3$ is a readily removable carboxy protecting group or a pharmaceutically acceptable salt-forming group or in vivo hydrolyzable ester group;

R$^4$ represents hydrogen or up to four substituents, which may be present on any of the carbon atoms in the ring system shown, selected from C$_{1-6}$ alkyl, C$_{2-6}$ alkenyl, alkynyl, C$_{2-6}$ alkoxy, hydroxy, halogen, amino, C$_{2-6}$ alkylamino, acylamino, di(C$_{1-6}$alkyl)amino, CO$_2$R, CONR$_2$, SO$_2$NR$_2$ where R is hydrogen or C$_{1-6}$ alkyl, aryl or heterocyclyl, which may be the same or different and wherein any R$^4$ alkyl substituent is optionally substituted by one or more substituents selected from the list from which R$^4$ is selected;

X is S, SO or SO$_2$; Y is S, SO or SO$_2$; n is 0 or 1; and m is 1 or 2;

wherein said alkyl, alkenyl and alkynyl each are straight and branched chain groups;

said aryl is phenyl or naphthyl, each of which may be substituted with up to five groups selected from halogen, mercapto, $(C_{1-6})$ alkyl, phenyl, $(C_{1-6})$ alkyl, hydroxy, amino, nitro, carboxy, $(C_{1-6})$ alkylcarbonyloxy, $(C_{1-6})$ alkoxycarbonyl, formyl, or $(C_{1-6})$ alkylcarbonyl groups; and wherein said heteroaryl is a heteroaromatic heterocyclic ring or ring system, having 5 or 6 ring atoms in each ring;

(Ia)

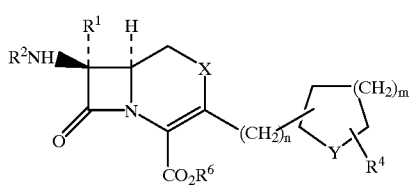

wherein $R^1$, $R^2$, $R^4$, m, n, X and Y are as defined with respect to formula (I) and the group $CO_2R^6$ is $CO_2R^3$ where $CO_2R^3$ is a carboxy group or a carboxylate anion, comprising the step of cyclising a compound of formula (IX):

(IX)

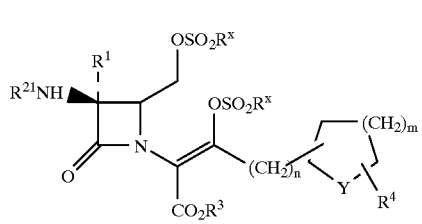

wherein Y, $R^1$, $R^4$, and m, n, and $CO_2R^3$ are as hereinbefore defined; each $R^x$ may be the same or different and is independently selected from $(C_{1-6})$alkyl or aryl; and $R^{21}$ is a group $R^2$ as hereinbefore defined or is an amino-protecting group or is a group which permits acylation to take place, and thereafter if necessary or desired, carrying out one or more of the following steps:

i) removing any protecting groups as defined with respect to formula (I) and (Ia);
ii) converting the group $CO_2R^3$ into a different group $CO_2R^3$, wherein the substitutent from which $R^3$ is selected is different;
iii) converting the group $R^{21}$ into a different group $R^{21}$, wherein the substituent from which $R^{21}$ is selected is different;
iv) converting the group Y into a different group Y wherein the substitutent from which Y is selected is different; and
v) converting the product into a salt.

2. A process for the preparation of a compound of formula (I) as defined in claim 1 and (II)

(II)

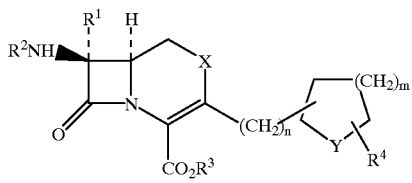

wherein $R^1$, $CO_2R^3$, $R^4$, m, n, X and Y are as defined with respect to formula (I), wherein any reactive groups may be protected, and wherein the amino group is optionally substituted with a group which permits acylation to take place, in which X is O comprising cyclising a compound of formula (VIII)

(VIII)

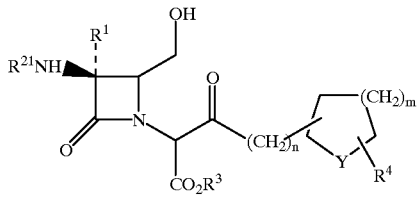

wherein Y, $R^1$, $R^4$, $R^{21}$, m, n, and $CO_2R^3$ are as defined with respect to formula (I), then thereafter if necessary or desired, comprising out one or more of the following steps:

i) removing any protecting groups as defined with respect to formula (I) and (II);
ii) converting the group $CO_2R^3$ into a different group $CO_2R^3$; wherein the substitutent from which $R^3$ is selected is different;
iii) converting the group $R^{21}$ into a different group $R^{21}$; wherein the substitutent from which $R^{21}$ is selected is different;
iv) converting the group Y into a different group Y; wherein the substituent from which Y is selected is different; and
v) converting the product into a salt.

\* \* \* \* \*